(12) United States Patent
Baxter, Jr.

(10) Patent No.: US 6,317,080 B1
(45) Date of Patent: Nov. 13, 2001

(54) EARLY DETECTION AND TRACKING SYSTEM FOR HAZARDOUS AIRBORNE SUBSTANCES

(76) Inventor: John Francis Baxter, Jr., 1083 N. Collier #248, Marco Island, FL (US) 34145

( * ) Notice: Subject to any disclaimer, the term of this patent is extended or adjusted under 35 U.S.C. 154(b) by 0 days.

(21) Appl. No.: 09/565,941

(22) Filed: May 5, 2000

(51) Int. Cl.[7] ........................................... G01S 1/00
(52) U.S. Cl. .......................... 342/357.09; 342/357.07; 244/31; 244/98
(58) Field of Search ..................... 342/357.09, 357.1, 342/357.17, 357.07; 244/31, 94, 97, 98

(56) References Cited

U.S. PATENT DOCUMENTS

| | | |
|---|---|---|
| H1916 * | 11/2000 | Hollander .................. 367/118 |
| 4,042,882 | 8/1977 | Camacho et al. . |
| 4,494,714 | 1/1985 | Hill et al. . |
| 4,564,159 | 1/1986 | Hill et al. . |
| 4,911,379 | 3/1990 | Kopelman . |
| 5,548,283 | 8/1996 | Martin . |
| 5,634,427 | 6/1997 | Rollins . |
| 5,636,480 | 6/1997 | Lauritsen et al. . |
| 5,645,248 * | 7/1997 | Campbell .................. 244/30 |
| 5,654,692 | 8/1997 | Baxter, Jr. et al. . |

* cited by examiner

Primary Examiner—Theodore M. Blum
(74) Attorney, Agent, or Firm—Anton J. Hopen; Smith & Hopen, P.A.

(57) ABSTRACT

A method of tracking airborne substances including the steps of detecting the presence of one or more airborne substances and releasing a tracking balloon into the path of the one or more airborne substances, the tracking balloon having a transmission means and a global positioning means adapted to communicate the latitude and longitude coordinates of the tracking balloon whereby the latitude and longitude coordinates of the tracking balloon are representative of the latitude and longitude of the one or more airborne substances previously detected.

18 Claims, 8 Drawing Sheets

EARLY DETECTION AND TRACKING SYSTEM FOR HAZARDOUS AIRBORNE SUBSTANCES

FIELD OF INVENTION

The present invention relates generally to a method and apparatus for tracking airborne substances, and more particularly, a method and apparatus for providing early warning and positioning data for hazardous airborne substances for military and civilian applications.

BACKGROUND OF THE INVENTION

When the wind shifted on the afternoon of Apr. 22, 1915, on fields near Ypres, France, the Imperial German Army ushered in a dangerous new era in warfare. World War I (1914–1918) had become a standoff of opposing infantries fighting from trenches. To break the stalemate, the German Supreme Command made a decision to change strategy. At 5 p.m. German combat engineers opened 5730 cylinders of compressed chlorine gas. Blown by the wind, this yellowish-green cloud wafted across the battlefield toward the unprepared Allied lines. Surrounded and choking from the unexplained gas, French and Belgian troops in the trenches turned and ran for their lives. Unopposed, but wary of the ominous cloud, the German infantry advanced a few hundred meters toward Allied lines and then dug in for the night.

Airborne hazards, whether by warfare, terrorism, industry or nature occurrences represent an ever-present threat to military and civilian personnel. Airborne hazards can be roughly divided into three main categories: nuclear, biological and chemical. A large nuclear explosion (half a megaton, or more) injects most of its fallout particles and gases into the stratosphere, above the tops of clouds and above the altitudes at which removal of contaminants from the atmosphere by scavenging takes place. Very small particles in the stratosphere do not reach the ground before they are blown at least several thousand miles. Most of these tiny particles remain airborne for weeks to years, are very widely dispersed, and are blown around the world several to many times before being deposited. By then the radioactivity of iodine-131 (that has a half life of only a little more than 8 days) is so greatly reduced that it is not nearly as dangerous as is radioactive iodine deposited much sooner with the fallout from smaller weapons of several hundred kilotons, or less, explosive power.

Nuclear explosions smaller than about half a megaton (500 kilotons) inject all or most of their fallout to lower altitudes—within the troposphere, below the stratosphere. Most of such fallout is deposited during the radioactive cloud's first world-circling trip, when even quite rapidly decaying radioiodine still is dangerously radioactive. This greater danger from smaller nuclear weapons has been proved by numerous measurements of fallout from many nuclear test explosions, both foreign and American.

The cloud from the steam explosion that blew off the roof and otherwise damaged the Chernobyl reactor building, may have risen quite soon to 20,000 feet or more and was partially blown eastward clear across Asia and the Pacific Ocean. However, the top of the radioactive smoke cloud over the Chernobyl power plant, that burned for days, rose only about 3,000 feet above the ground. As a result, much of the airborne Chernobyl radiation stayed at relatively low altitudes where scavenging (removal) of smoke and fallout particles and gasses is most effective and rapid, due to aggregation on cloud droplets, rain-out, and dry deposition. In contrast, almost all of the fallout particles and radioactive gasses from a nuclear explosion are injected much higher, to altitudes where scavenging is less effective; there, the generally prevailing west-to-east winds promptly start transporting very small particles and radioactive gasses (that originate in the mid-latitudes of the northern hemisphere) around the world.

Variable winds for days carried much of the Chernobyl radioactive material northward to Scandinavian countries, then westward and southward to other European countries. The resultant wide dispersal of this fallout allowed time for both scavenging and radioactive decay before a small fraction of these invisible radioactive clouds rose and also were blown eastward by the prevailing high-altitude winds. These west winds carried an extremely small fraction of the radioactive emissions from the burning Chernobyl plant clear across Asia and the Pacific to America.

Accordingly, it can be clearly understood that early and precise tracking of radioactive fallout is critical. Before significant radioactive decay occurs and while the particles are particularly lethal, it would advantageous to track the early dispersion pattern at lower altitudes as fallout at that level would be more prone to make contact with populations. However, low-level winds are often difficult to track by satellite and numerous ground-based detectors are required to predict time-to-intercept and location data for such fallout.

Chemical weapons (herein "CW") release toxic gases or liquids that attack the body's nerves, blood, skin or lungs. They may produce surface effects such as tears, blistering, or vomiting, or cause hallucinations or loss of nervous control. Chemical attacks can contaminate an area for between several hours and several days, compromising equipment and forcing troops to wear highly restrictive protective clothing or take chemical antidotes whose side effects remain largely unknown. Chemical attacks cause widespread panic amongst both military and civilian populations, and their terror effects on civilians are potent. The large number of potential casualties places burdens on medical facilities and can overwhelm stretched military resources.

CW agents are frequently called war gases and a war where CW agents are used is usually called a gas war. These incorrect terms are a result of history. During the First World War use was made of chlorine and phosgene which are gases at room temperature and normal atmospheric pressure. The CW agents used today are only exceptionally gases. Normally they are liquids or solids. However, a certain amount of the substance is always in volatile form (the amount depending on how rapidly the substance evaporates) and the gas concentration may become poisonous. Both solid substances and liquids can also be dispersed in the air in atomized form, so-called aerosols. An aerosol can penetrate the body through the respiratory organs in the same way as a gas.

Chemical weapons depend more than any other armament upon atmospheric and topographical factors, whilst temperature, weather and terrain are important factors in determining the persistence of a given chemical agent. Large quantities of agents are required to achieve high lethality, and most chemical agents degrade rapidly, allowing areas, buildings and equipment affected to be reused (even if they require decontamination first). An attacker's use of persistent agents may mean that areas an attacker wishes to move across or occupy remain contaminated, necessitating the use of protective equipment or decontamination for attacking forces.

Chemical weapons can be delivered by a wide range of weapons systems, including ballistic and cruise missiles, combat aircraft-delivered bombs, artillery shells and land mines. According to the U.S. General Accounting Office, during the Iran-Iraq war, Iraq delivered mustard gas and tabun with artillery shells, aerial bombs, missiles, rockets, grenades, and bursting smoke munitions. The Soviet-made Scud-B and FROG-7 can deliver warheads bulk-filled with chemical agent and Iraq developed, deployed, but did not use, chemical warheads on its modified Scud missiles during the Gulf War. North Korea is also believed to have developed chemical warheads for its Scud B and Scud C ballistic missiles.

The most lethal chemical warfare agents are nerve agents, such as sarin, tabun, and VX, which produce convulsions and death by blocking an enzyme (acetylcholinesterase) needed to transmit messages in the nervous system. Nerve agents can be lethal in minute amounts: A tiny drop of VX on the skin, for example, can overcome an adult human in a matter of minutes.

Technologically, chemical and biological weapons are almost entirely different. Chemical weapons are highly toxic, manufactured substances that can be disseminated as vapors, aerosols, or liquids. Biological weapons, on the other hand, are living, disease-causing microorganisms or toxins (deadly chemicals derived from living organisms) which, in their most effective form, are disseminated as aerosols that are inhaled.

Biological weapons (excluding toxins, which resemble chemical weapons) consist of living, infectious microorganisms that are disseminated as aerosols through the atmosphere. Inhaled into the lungs, biological agents begin to multiply within the body, causing a disease that can incapacitate or kill the victim. Biological warfare aerosols are generally invisible, odorless, and tasteless. The onset of symptoms is usually delayed, often for as much as three to five days, so the victim of biological warfare may not even know that an attack has occurred until the disease has reached an advanced stage.

The worst outbreak of anthrax occurred in 1979, when a biological weapons plant in Sverdlovsk, Russia (present-day Yekaterinburg), accidentally released airborne anthrax spores, killing 66 people. In 1998 American scientists at Los Alamos National Laboratory used newly developed techniques to determine that the spores released in the accident contained at least four different strains of anthrax. This raised concerns that Russia, and possibly other countries, may be working on a vaccine-resistant form of anthrax for use as a biological weapon. The United States government had previously planned to vaccinate all American personnel against anthrax; however, the possibility of genetically engineered new forms of the disease currently has scientists divided as to the effectiveness of such a vaccine.

Airborne threats are not limited to warfare or terrorism. Industrial accidents releasing toxins into the atmosphere require advanced detection and precise tracking to provide emergency response services. Natural disasters such as volcanic eruptions and forest fires produce airborne hazards wherein altitude level-tracking is desirable. In effect, the detection and tracking airborne substances may simply be a prelude to an additional ground-based threat as is the case in large-scale forest fires.

Thus, nuclear, chemical, biological and naturally occurring airborne dangers may threaten military and civilian populations. In those circumstances, it is important to provide early detection and warning services for medical, rescue and countermeasure operations. However, current satellite and ground-based methods are woefully ineffective in tracking low-altitude airborne hazards. Sudden wind shifts, topography and other factors greatly effect the direction and dissemination of airborne particles. What is needed is a new method and apparatus for tracking such hazards.

A method anticipated in the current invention utilizes the inherent advantages of balloons. Such advantages include low cost, minimal mechanical complexity, and more particularly, the fact that a balloon's direction of travel is substantially the same as that of the hazardous airborne substances. Accordingly, if an unmanned balloon is launched into a field of hazardous airborne substances, the balloon's position will substantially match that of the hazardous airborne substances.

It is notoriously well known that balloons have been used to transmit environmental data. For decades, weather balloons have been used in the measurement and evaluation of mostly upper atmospheric conditions. Information may be obtained during the vertical ascent of the balloon through the atmosphere or during its motions once it has reached a predetermined maximum altitude. Weather balloons are most often inflated with helium which is less dense than air. Atmospheric pressure, temperature and humidity information may be sent by radio from a balloon.

However, in view of the prior art in at the time the present invention was made, it was not obvious to those of ordinary skill in the pertinent art how the identified needs could be fulfilled.

SUMMARY OF THE INVENTION

The present invention solves significant problems in the art by providing a method of tracking airborne substances comprising the steps of detecting the presence of one or more airborne substances and releasing a tracking balloon into the path of the one or more airborne substances, the tracking balloon having a transmission means and a global positioning means adapted to communicate the latitude and longitude coordinates of the tracking balloon whereby the latitude and longitude coordinates of the tracking balloon are representative of the latitude and longitude of the one or more airborne substances previously detected.

Balloons are capable of maintaining a wide span of altitudes from ground-level to 90,000 feet. Various airborne substances drift at different altitudes depending on a variety of factors. In a preferred method, the one or more airborne substances is associated with a predetermined optimal tracking altitude and an altitude adjustment means is provided to match the altitude of the tracking balloon with the predetermined optimal tracking altitude. The altitude adjustment means may be embodied by several methods. One method comprises the steps of inflating the tracking balloon with a low density gas such as helium or hydrogen wherein the pressure inside and outside the tracking balloon is substantially the same and control of the altitude of the tracking balloon is achieved by gas release and ballast drops.

An alternative method of controlling altitude comprises the steps of constructing the tracking balloon of a non-extensible envelope material having a substantially high elasticity modulus and inflating the tracking balloon with a low density gas to a pressure higher than the ambient pressure wherein the volume of the tracking balloon remains essentially constant. By the time the balloon reaches it constant-density level, the free-lift gas has become pressurized. Variations in pressure caused by the heat of the sun produce changes in the internal gas pressure. However, the volume of the balloon remains fixed and thereby floats at a constant level. In any case, the altitude adjustment means is fundamentally controlled by an altimeter or by sonic or light-based measurements from tracking balloon to earth surface.

The release of the tracking balloon may be initiated by manual control locally or by remote communication such as satellite, radio-frequency or the like. Alternatively, an automatic release method may be provided comprising the steps of preselecting one or more airborne substances sought to be monitored, providing an unmanned, empirical measuring means for the one or more airborne substances, preselecting a threshold trigger level for the one or more airborne substances and releasing the tracking balloon upon the detection of the threshold trigger level of the one or more airborne substances.

A preferred embodiment of invention comprises the steps of transmitting the latitude and longitude coordinates to a CPU means, computing the speed and direction of the tracking balloon based on a plurality of latitude and longitude coordinates obtained at different times and resolving an anticipated path for the tracking balloon.

A two-way positioning device is provided having a global positioning means for determining the latitude and longitude of the two-way position device and a transmission receiving means for obtaining the current latitude and longitude of the tracking balloon. An additional feature of the method provides the step of resolving time-to-intercept data between the two-way positioning device and the tracking balloon.

A preferred embodiment provides for the transmission of the latitude and longitude coordinates of the tracking balloon to a two-way positioning device having a global positioning means for determining the latitude and longitude of the two-way position device and a transmission receiving means for obtaining the current latitude and longitude of the tracking balloon, computing the speed and direction of the tracking balloon based on a plurality of latitude and longitude coordinates obtained at different times, and resolving an anticipated path for the tracking balloon.

As an apparatus, the invention may be described as comprising a balloon station housing enclosing a compacted tracking balloon, a gas conduit in fluid communication with the compacted tracking balloon and a compressed lighter-than-air fluid reservoir, an inflation release mechanism responsive to a triggering signal for allowing fluid to flow through the gas conduit, a control circuit for sending the triggering signal, a global positioning means adapted to resolve an array of latitude and longitude coordinates of the tracking balloon, and a transmission means for relaying the array of latitude and longitude coordinates to a remote receiver. The lighter-than-air fluid is meant to include gaseous fluids such as hydrogen, helium or the like.

The control circuit may be activated by a remote signal upon the manual determination that the balloon should be released. Providing a remote activation to the control circuit permits the release of the balloon without requiring an operator to be placed in harm's way. Alternatively, the control circuit may be activated by a particulate detection means. Such particulate detection means are well-known in the art and include gas chromatography, IR spectrum analysis, fluorescence-based fiber optic biosensors and other instruments calibrated to automatically detect the presence of preselected substance.

As many substances are relative benign at lower concentrations while lethal at high concentrations, it is preferred that the particulate detection means be pre-configured to activate the control circuit when a predetermined particle concentration threshold is detected.

An altitude control means may comprise a gas release means and ballast drop means, or constructing the tracking, balloon of an non-extensible envelope material having a high elasticity modulus wherein the volume of the tracking balloon flies a path of constant density in the atmosphere.

A computer processor may be incorporated to control the altitude control means having a CPU means in electronic communication with the altitude control means and the particulate detection means, a memory means in electronic communication with the CPU mean, the memory means storing an array of optimal altitudes for at least one or more target airborne substances wherein the particulate detection means communicates the identity of at least one or more airborne substances meeting the predetermined particle concentration threshold to the CPU means which, in turn, obtains an optimal altitude value from the memory means, the CPU means therein controlling the inflation release mechanism to pressurize the tracking balloon to achieve an optimal altitude.

A problem encountered with automatic balloon inflation is that of early liftoff. When the balloon is partially inflated, it is subject to winds which would allow the balloon to drag along the ground, damaging the sensitive equipment before full inflation can be achieved. In order to overcome this problem a preferred embodiment of the invention comprises a balloon station housing enclosing a compacted tracking balloon and a base securely fixing the balloon station housing to a substantially immovable surface. The substantially immovable surface may be on the ground, on a smoke stack, in a tower, on a ship depending on the desired application. Substantially immovable should be understood to be sufficiently stable to prevent movement during the inflation of the tracking balloon. A retention means having a closed state and an open state securely couples the compacted tracking balloon to the base when the retention means is in the closed state. A control circuit in electronic communication with the inflation release mechanism and the retention means provides control of the system wherein upon substantially full inflation of the tracking balloon the control circuit directs the retention means to the open state thereby uncoupling the tracking balloon from the base wherein the tracking balloon rises up and away from the base at substantially full buoyancy.

The retention means may comprise a retention solenoid securely coupling the compacted tracking balloon to the base when the retention solenoid is in a non-energized state. A power source in communication with the retention solenoid and in electronic communication with the control circuit is provided wherein upon substantially full inflation of the tracking balloon the control circuit links the power source to the retention solenoid thereby energizing the solenoid to uncouple the tracking balloon from the base wherein the tracking balloon rises up and away from the base at substantially full buoyancy.

Accordingly, it is an object of the present invention to provide a method and apparatus for precisely detecting, monitoring and tracking the drift direction of airborne substances.

It is another object of the present invention to provide a method and apparatus for providing real-time, precise information regarding the location, drift and time-to-intercept of hazardous airborne substances for military and civilian populations.

It is another object of the present invention to measure and track the drift of hazardous airborne substances without requiring human intervention in proximity to the hazard.

It is another object of the invention to provide an early warning perimeter detection and tracking system against nuclear, biological or chemical aggression.

It is another object of the invention to provide an automatic tracking balloon inflation and release mechanism that prevents damage to sensitive tracking equipment.

An advantage of the invention is that accurate positioning data may be obtained on the location and drift of hazardous airborne substances without required manual human readings to be performed.

Another advantage of the invention is that global positioning data from both the tracking balloon location and portable ground-level based units may be cross-referenced to determine the relative location of the hazardous airborne substances and calculate time-to-intercept data.

Another advantage of the invention is that potentially hazardous areas such as industrial plants, war zones, terrorism targets and the like may be configured with one or more units of the invention to provide a quick response and detection platform.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
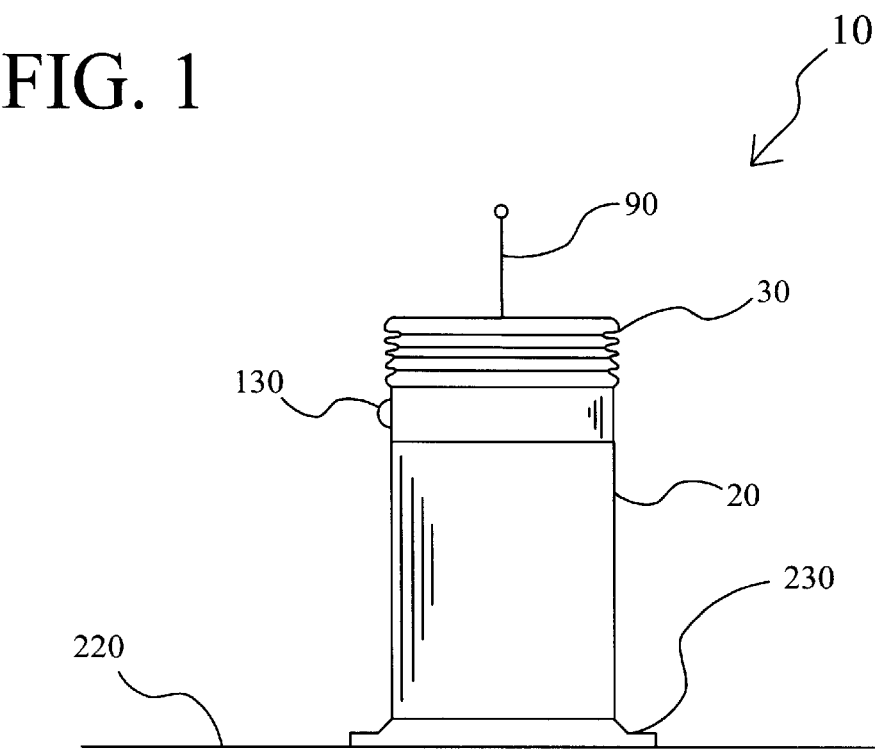
FIG. 1 is a side elevational view of the invention housing prior to release of the tracking balloon.
Figure 2:
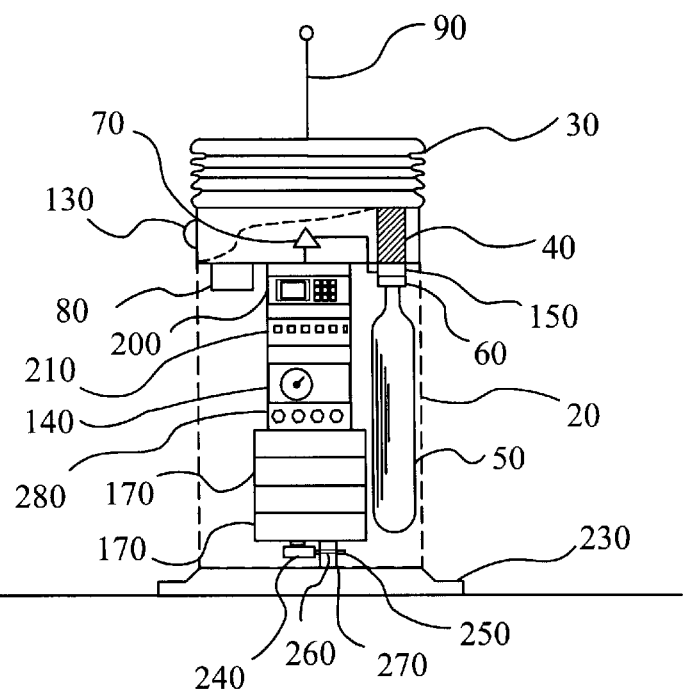
FIG. 2 is a side elevational, partially sectional view of the invention prior to the release of the tracking balloon.
Figure 3:
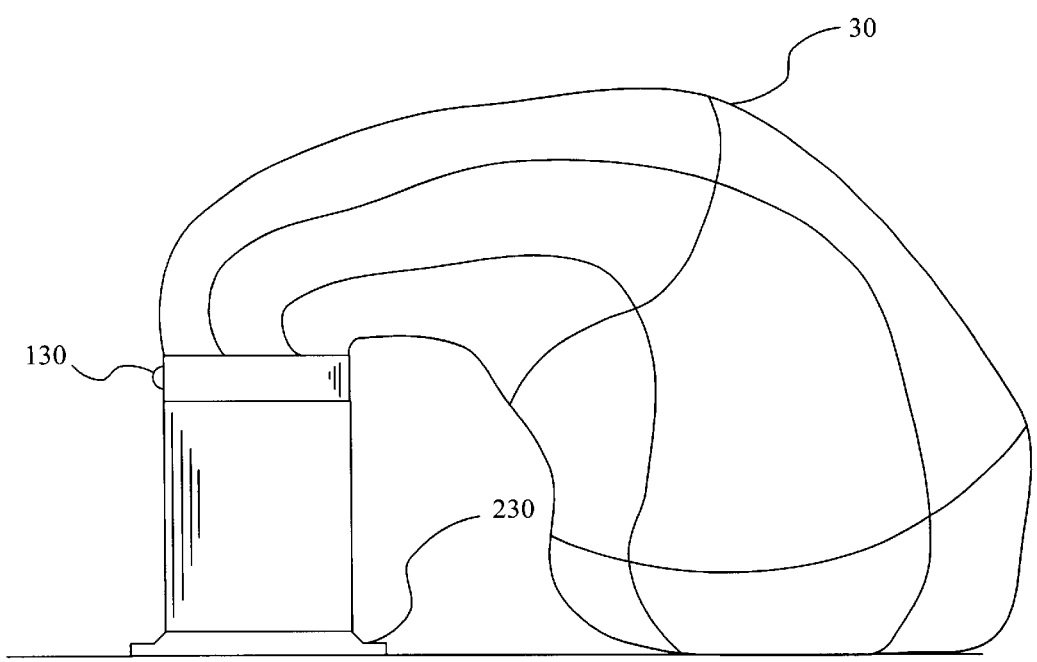
FIG. 3 is a side elevational view of the tracking balloon at partial inflation and before release.
Figure 4:
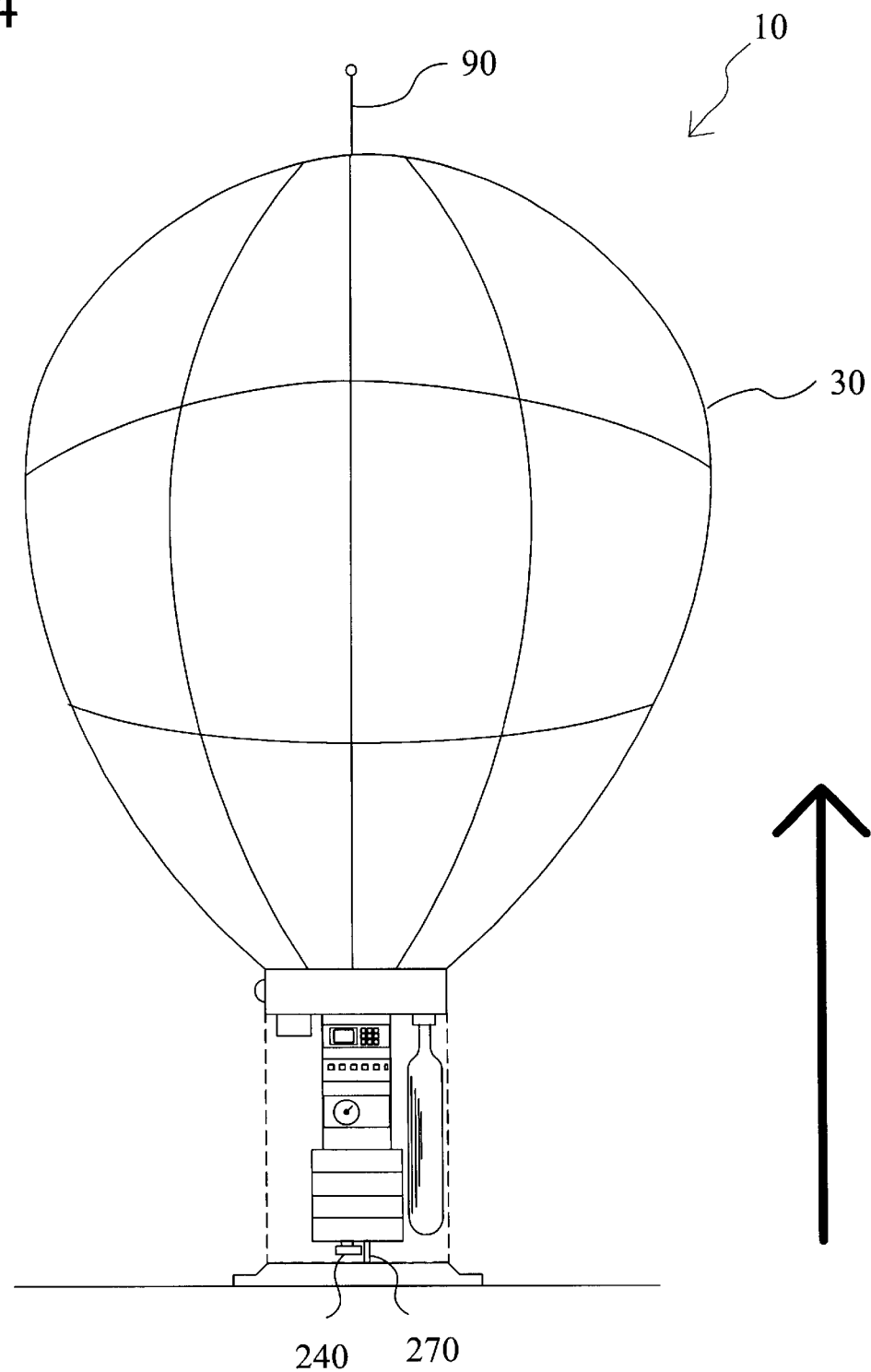
FIG. 4 is a side elevational, partially sectional view of the tracking balloon fully inflated and the release solenoid withdrawn from the retention bracket.
Figure 5:
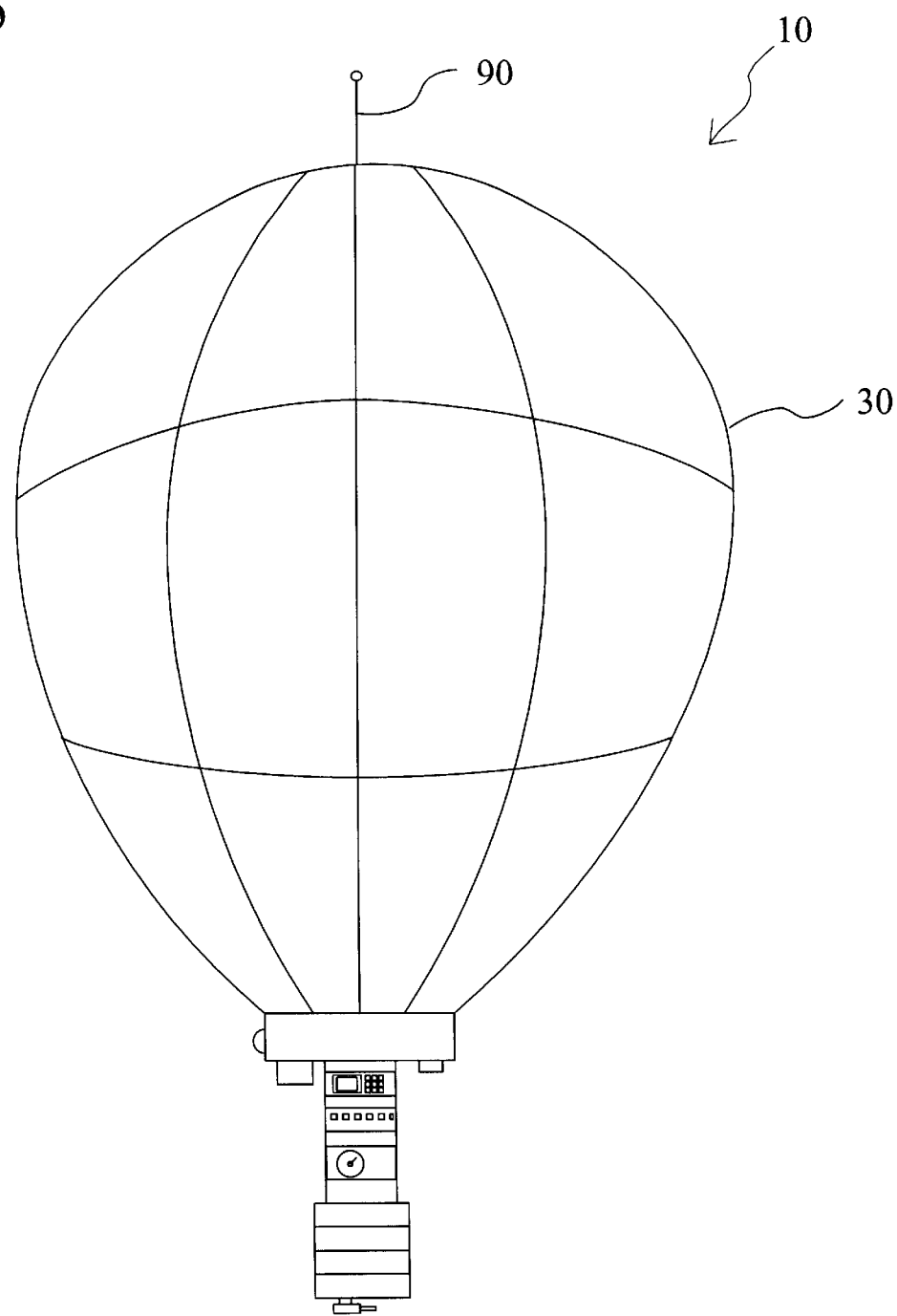
FIG. 5 is a side elevational view of the tracking balloon in flight.

Referring initially to FIGS. 1 and 2, it will there be seen that an illustrative embodiment of the present invention is denoted by the reference number 10 as a whole.

Figure 7:
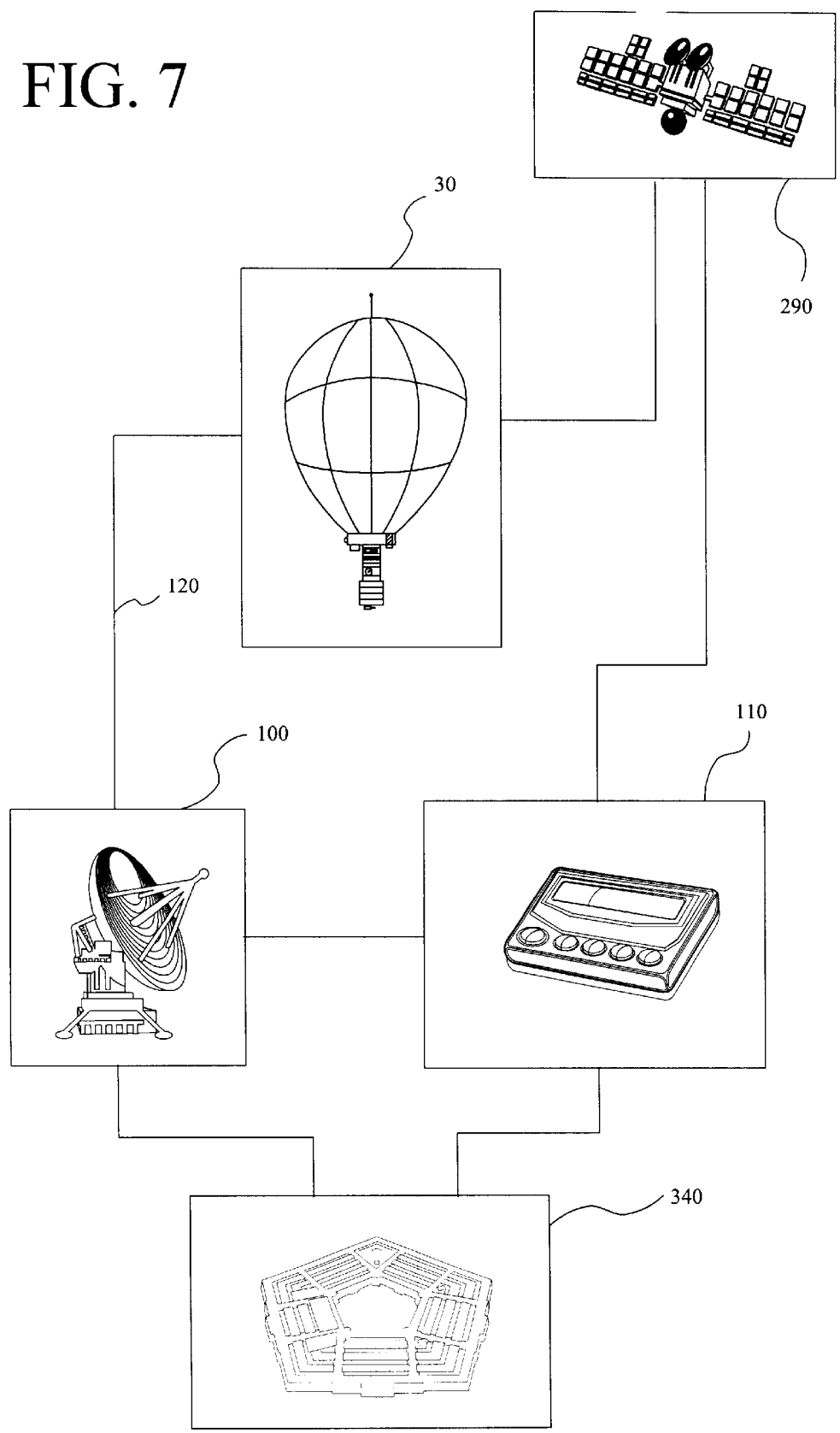
FIG. 7 is a diagrammatic view of the global positioning relay method of the invention.

A cylindrical balloon station housing 20 encloses a compacted tracking balloon 30. A gas conduit 40 is positioned in fluid communication between the tracking balloon 30 and a compressed lighter-than-air fluid reservoir 50. An inflation release mechanism 60 is responsive to a triggering signal for allowing fluid to flow through the gas conduit 40. A control circuit 70 is provided for sending the triggering signal. A global position means 80 is provided for resolving an array of latitude and longitude coordinates of the tracking balloon 30 during flight and a transmission means 90 relays the array of latitude and longitude coordinates to a remote receiver 100 (FIG. 7). The control circuit 70 may be activated by a remote signal 120 transmitted to initiate launch of the tracking balloon or may be activated by a particulate detection means 130 pre-configured to activate the control circuit 70 when a predetermined particle concentration threshold is detected.

Figure 6:
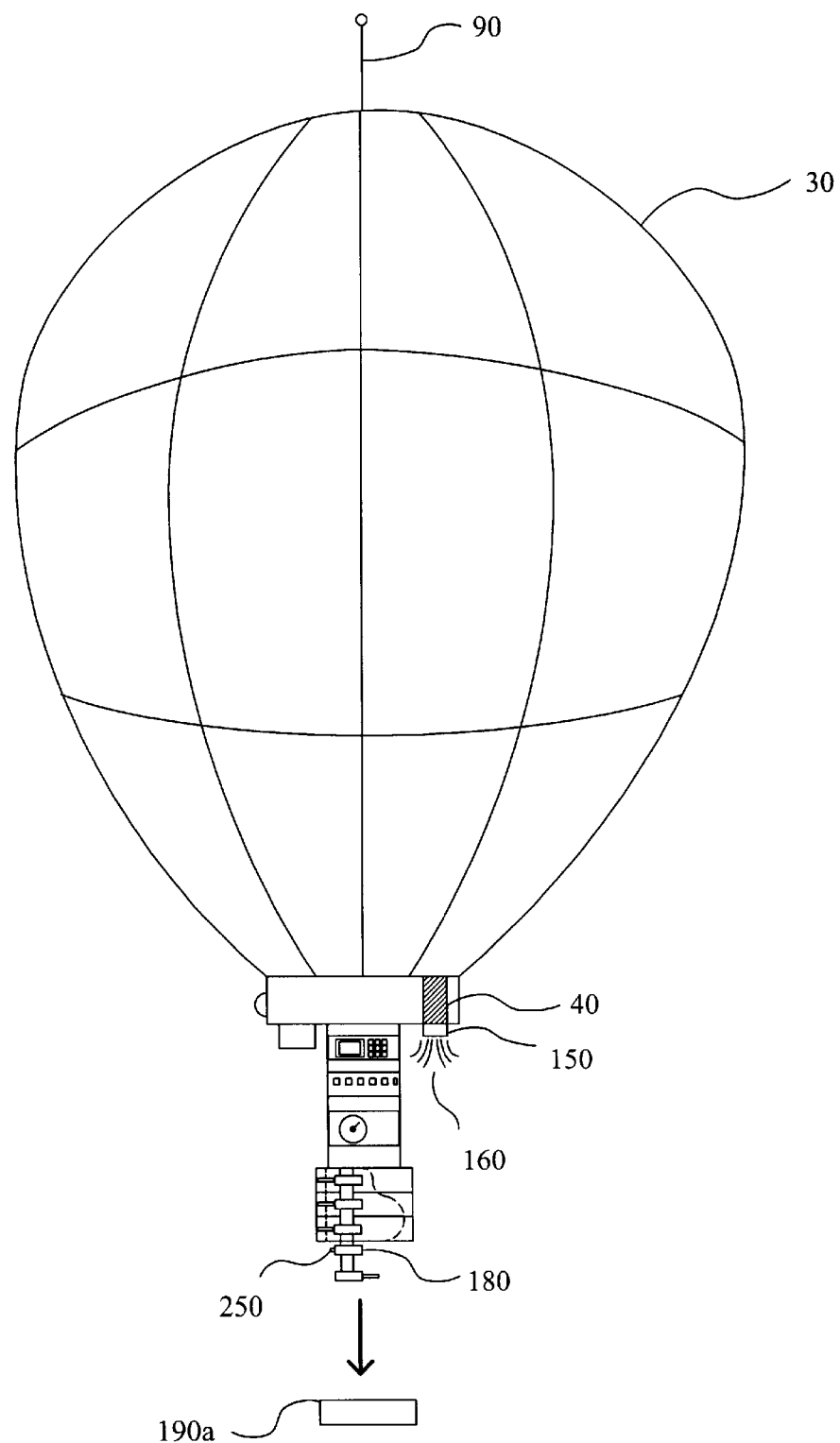
FIG. 6 is a side elevational, partially sectional view of the tracking balloon releasing a ballast and expelling gas.

In a preferred embodiment, the level of flight for the tracking balloon 30 is controlled by an altitude control means 140. In one embodiment of the invention, the altitude control means 140 comprises a gas release means 150 wherein pressurized gas within the tracking balloon 30 may be released 160 (FIG. 6) to decrease buoyancy, and thereby altitude of the apparatus while in flight. Should an increase in altitude be desired, ballast drop means 170 may be provided wherein ballast is released as shown in FIG. 6 wherein at least one or more solenoids 180 having a retention bolt 250 are energized to withdraw the retention bolt 250 out of an aperture on the inside of the ballast means 170 thereby releasing the ballast 190a and increasing altitude.

A CPU means 200 in electronic communication with said altitude control means 140 accesses a memory means 210 storing an array of optimal altitudes for at least one or more target airborne substances. The particulate detection means 130 communicates the identity of at least one ore more airborne substances meeting the predetermined particle concentration threshold to the CPU means 200 which, in turn, obtains an optimal altitude value from the memory means 210. The CPU then controls the inflation release mechanism 60 to pressurize the tracking balloon only the to point necessary to achieve an optimal altitude.

The balloon station housing 20 is securely fixed to a substantially immovable surface 220 by a base 230. A retention solenoid 240 securely couples the tracking balloon 30 to the base 230 when the retention solenoid 240 is in a non-energized state. A retention bolt 250 biased outward from the retention solenoid 240 is received through an aperture 260 in a retention bracket 270 mounted to the base 230. A power source 280 in communication with the retention solenoid 240 and in electronic communication with the control circuit 70 wherein upon substantially full inflation of the tracking balloon, the control circuit 70 links the power source 280 to the retention solenoid 240 thereby energizing the solenoid to withdraw the retention bolt 250 from the aperture 260 in the retention bracket 270 wherein the tracking balloon 30 rises up and away from the base 230 and housing 20 at substantially full buoyancy.

It can be seen from FIG. 3 that premature release of the tracking balloon under partial inflation would be undesirable, as the insufficient buoyancy of the tracking balloon would lead to the electronic equipment dragging on the surface. The benefit of the retention solenoid 240 is further illustrated in FIG. 4 wherein the tracking balloon 30 has achieved fall inflation and, accordingly, the retention bolt 250 has been withdrawn from the retention bracket 270 thereby allowing the tracking balloon 30 to lift off at substantially full buoyancy clear of the balloon station housing 20 as illustrated in FIG. 5.

FIG. 7 illustrates the pathway of global positioning data wherein a global positioning satellite 290 is used to determine both the latitude and longitude of the tracking balloon 30 and a two-way positioning device 110. Position information is relayed from the tracking balloon 30 to a transmission receiving means 100 which communicates the data to the two-way positioning device 110. The speed and direction of the tracking balloon based on a plurality of latitude and longitude coordinates obtained at different times resolves an anticipated path for the tracking balloon 30. This anticipated path is then compared to the latitude and longitude data in the two-way position device 110 to resolve a time-to-intercept calculation. This permits ground troops and civilian rescue personnel to have precise and real-time information regarding their proximity to an airborne hazard. In addition, global positioning coordinates of the two-way positioning device may be transmitted to a central command center 340 thereby providing a strategic overview of personnel deployment locations for military and civilian operations.

Figure 8:
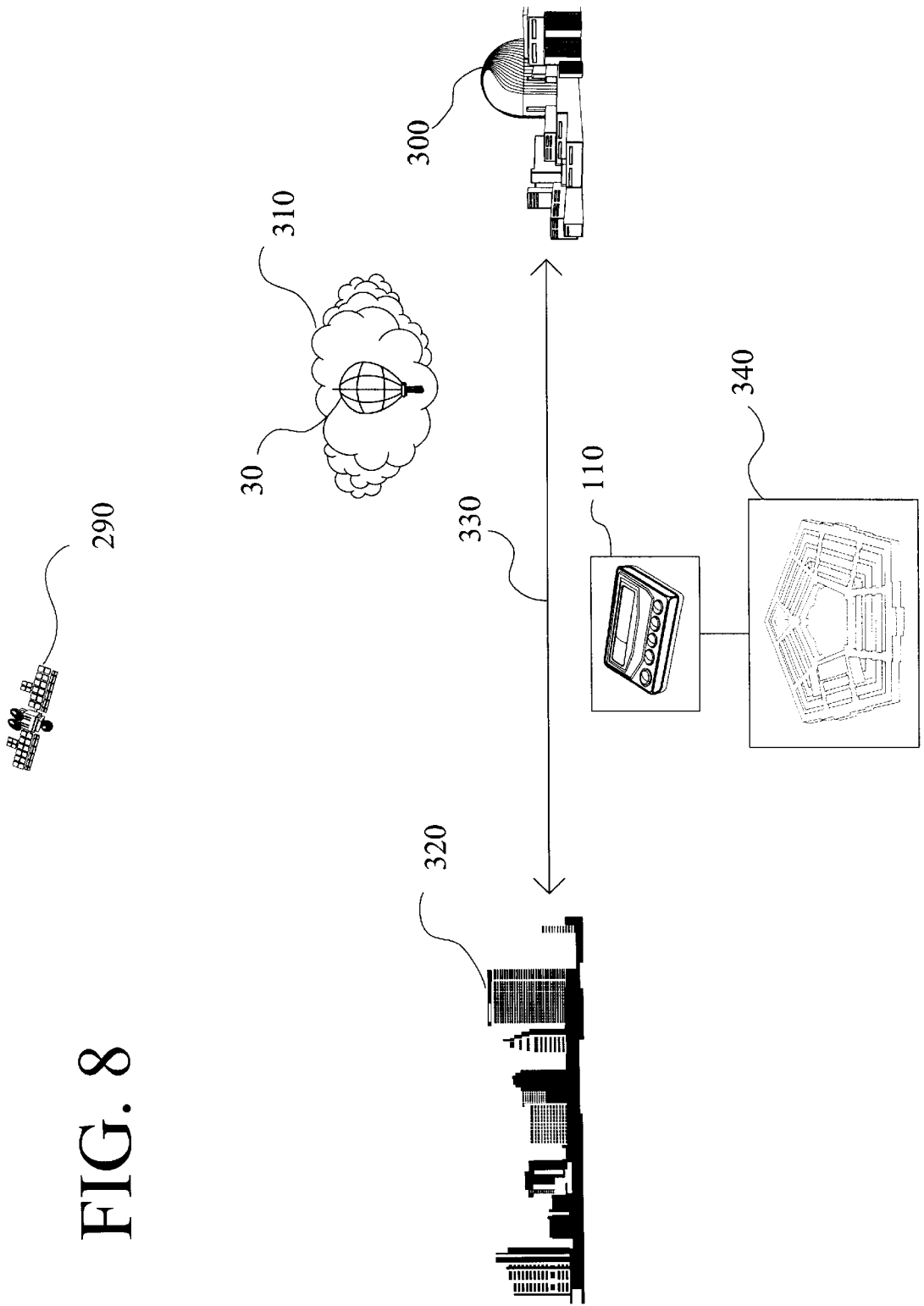
FIG. 8 is a diagrammatic view of the global positioning relay method of the invention in as applied in a nuclear fallout scenario.

FIG. 8 illustrates an application for the invention wherein a nuclear plant 300 releases a cloud of radioactive fallout material 310. Either by auto-detection or by manual activation, the tracking balloon 30 is released into the cloud 310. Winds, topography and other natural environmental factors dictate the drift, direction and speed of the cloud 30. However, heretofore unknown data is available through the novel invention by latitude and longitude information transmitted by the tracking balloon 30 during its flight. The proximity of the nuclear plant 300 and a populated area 320 is calculable 330. Furthermore, the present invention offers real-time data to determine location, speed and time-to-intercept calculations thereby permitting the populated area 320 to take appropriate measures.

Figure 9:
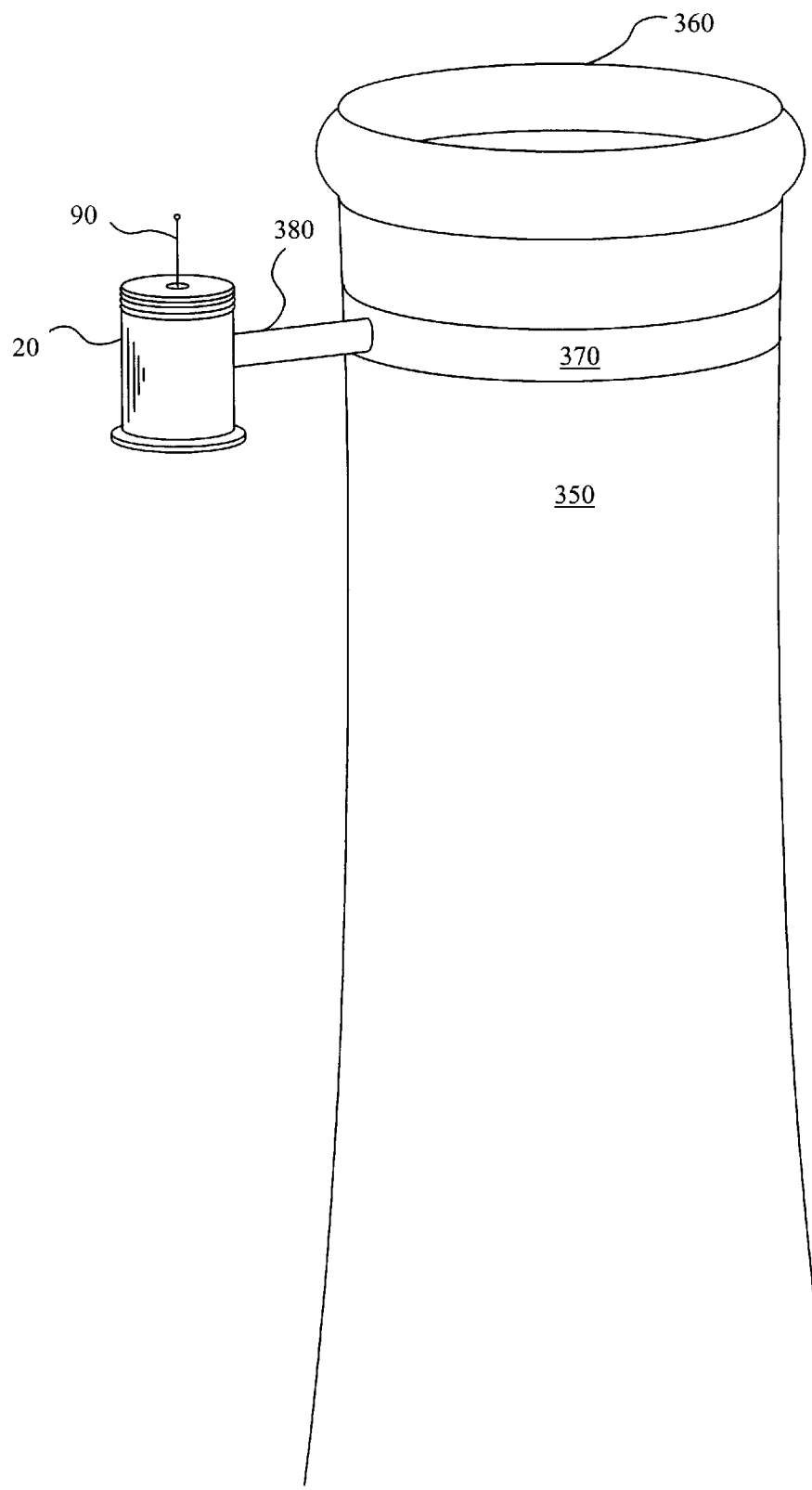
FIG. 9 is an illustrative embodiment of the invention secured to a smokestack.

FIG. 9 illustrates an embodiment of the invention for close-proximity monitoring of smokestack emissions. A smokestack 350 is fitting with a mounting means 370 in close proximity to the smokestack top 360. An elongate arm 380 secures the balloon station housing 20 away from the smokestack 350.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of tracking airborne substances comprising the steps of:
   a. detecting the presence of one or more airborne substances; and
   b. releasing a tracking balloon responsive to said detection into the path of said one or more airborne substances, said tracking balloon having a transmission means and a global positioning means adapted to communicate the latitude and longitude coordinates of said tracking balloon whereby the latitude and longitude coordinates of said tracking balloon are representative of the latitude and longitude of said one or more airborne substances previously detected.

2. The method of claim 1 further comprising the steps of:
   a. associating said one or more airborne substances with a predetermined optimal tracking altitude that is based on the airborne properties of said one or more airborne substances; and
   b. providing an altitude adjustment means to match the altitude of said tracking balloon with said predetermined optimal tracking altitude.

3. The method of claim 2 wherein said altitude adjustment means comprises the steps of:
   a. inflating said tracking balloon with a low density gas wherein the pressure inside and outside said tracking balloon is substantially the same; and
   b. controlling the altitude of said tracking balloon by gas release and ballast drops.

4. The method of claim 2 wherein said altitude adjustment means comprises the steps of:
   a. constructing said tracking balloon of an envelope material having a substantially high elasticity modulus; and
   b. inflating said tracking balloon with a low density gas to a pressure higher than the ambient pressure wherein the volume of said tracking balloon remains essentially constant.

5. The method of claim 1 wherein said detection of airborne substances comprises the steps of:
   a. preselecting one or more airborne substances sought to be monitored;
   b. providing an unmanned, empirical particle concentration measuring means for said one or more airborne substances;
   c. preselecting a threshold concentration trigger level for said one or more airborne substances; and
   d. initiating step b. of claim 1 upon the detection of said threshold concentration trigger level of said one or more airborne substances.

6. The method of claim 2 further comprising the step of providing a two-way positioning device having a global positioning means for determining the latitude and longitude of said two-way position device and a transmission receiving means for obtaining the current latitude and longitude of said tracking balloon.

7. The method of claim 6 further comprising the step of resolving time-to-intercept data between said two-way positioning device and said tracking balloon so that ground troops and civilian rescue personnel have precise and real-time information regarding their proximity to an airborne hazard.

8. An apparatus for tracking airborne substances comprising:
   a. a balloon station housing enclosing a compacted tracking balloon;
   b. a gas conduit in fluid communication with said compacted tracking balloon and a compressed lighter-than-air fluid reservoir;
   c. an inflation release mechanism responsive to a triggering signal for allowing fluid to flow through said gas conduit;
   d. a control circuit that is activated by a particulate detection means for sending said triggering signal;
   e. said particulate detection means is pre-configured to automatically activate said control circuit when a predetermined particle concentration threshold is detected;
   f. a global positioning means adapted to resolve an array of latitude and longitude coordinates of said tracking balloon; and g. a transmission means for relaying said array of latitude and longitude coordinates to a remote receiver.

9. The apparatus of claim 8 wherein said control circuit is activated by a remote signal.

10. The apparatus of claim 9 further comprising an altitude control means.

11. The apparatus of claim 10 wherein said altitude control means comprises gas release means and ballast drop means.

12. The apparatus of claim 10 wherein said altitude control means comprises constructing said tracking balloon of a non-extensible envelope material having a high elasticity modulus wherein the constant volume of said tracking balloon enables it to fly a path of constant density in the atmosphere.

13. The apparatus of claim 8 further comprising:

a. an altitude control means;

b. a CPU means in electronic communication with said altitude control means and said particulate detection means;

c. a memory means in electronic communication with said CPU mean, said memory means storing an array of optimal altitudes that are based on airborne properties for at least one or more target airborne substances wherein said particulate detection means communicates the identity of at least one or more airborne substances meeting said predetermined particle concentration threshold to said CPU means which, in turn, obtains an optimal altitude value from said memory means, said CPU means therein controlling said inflation release mechanism to pressurize said tracking balloon to achieve an optimal altitude.

14. An apparatus for tracking airborne substances comprising:

a. a balloon station housing enclosing a compacted tracking balloon;

b. a base securely fixing said balloon station housing to a substantially immovable surface;

c. a retention means having a closed state and an open state securely coupling said compacted tracking balloon to said base when said retention means is in said closed state;

d. a gas conduit in fluid communication with said compacted tracking balloon and a compressed lighter-than-air fluid reservoir;

e. a particulate detection means;

f. a triggering signal responsive to the particulate detection means;

g. an inflation release mechanism responsive to said triggering signal for allowing fluid to flow through said gas conduit;

h. a control circuit in electronic communication with said inflation release mechanism for sending said triggering signal and in electronic communication with said retention means;

wherein upon substantially full inflation of said tracking balloon said control circuit directs said retention means to said open state thereby uncoupling said tracking balloon from said base wherein said tracking balloon rises up and away from said base at substantially full buoyancy.

15. The apparatus of claim 14 further comprising:

a. a retention solenoid securely couples said compacted tracking balloon to said base when said retention solenoid is in a non-energized state;

b. a power source in communication with said retention solenoid and in electronic communication with said control circuit wherein upon substantially full inflation of said tracking balloon said control circuit links said power source to said retention solenoid thereby energizing said solenoid to uncouple said tracking balloon from said base wherein said tracking balloon rises up and away from said base at substantially full buoyancy.

16. The apparatus of claim 14 further comprising:

a. a global positioning means adapted to resolve an array of latitude and longitude coordinates of said tracking balloon; and b. a transmission means for relaying said array of latitude and longitude coordinates to a remote receiver.

17. A method of tracking airborne substances comprising the steps of:

a. detecting the presence of one or more airborne substances;

b. releasing a tracking balloon responsive to said detection into the path of said one or more airborne substances, said tracking balloon having a transmission means and a global positioning means adapted to communicate the latitude and longitude coordinates of said tracking balloon whereby the latitude and longitude coordinates of said tracking balloon are representative of the latitude and longitude of said one or more airborne substances previously detected;

c. transmitting said latitude and longitude coordinates to a CPU means;

d. computing the speed and direction of said tracking balloon based on a plurality of latitude and longitude coordinates obtained at different times; and e. resolving an anticipated path for said tracking balloon and said one or more airborne substances.

18. A method of tracking airborne substances comprising the steps of:

a. detecting the presence of one or more airborne substances;

b. releasing a tracking balloon responsive to said detection into the path of said one or more airborne substances, said tracking balloon having a transmission means and a global positioning means adapted to communicate the latitude and longitude coordinates of said tracking balloon whereby the latitude and longitude coordinates of said tracking balloon are representative of the latitude and longitude of said one or more airborne substances previously detected;

c. transmitting said latitude and longitude coordinates of said tracking balloon to a two-way positioning device having a global positioning means for determining the latitude and longitude of said two-way position device and a transmission receiving means for obtaining the current latitude and longitude of said tracking balloon;

d. computing the speed and direction of said tracking balloon based on a plurality of latitude and longitude coordinates obtained at different times; and e. resolving an anticipated path for said tracking balloon.

* * * * *